United States Patent [19]
Stojiljkovic et al.

[11] Patent Number: 6,066,628
[45] Date of Patent: May 23, 2000

[54] NON-IRON METALLOPORPHYRINS AND METHODS OF USE

[75] Inventors: Igor Stojiljkovic; Gordon G. Churchward, both of Atlanta, Ga.

[73] Assignee: Emory University, Atlanta, Ga.

[21] Appl. No.: 09/005,373

[22] Filed: Jan. 9, 1998

Related U.S. Application Data

[60] Provisional application No. 60/035,079, Jan. 9, 1997, abandoned.

[51] Int. Cl.⁷ .......................... A61K 31/40; C07D 487/22
[52] U.S. Cl. .......................... 514/185; 514/183; 514/410; 540/145
[58] Field of Search .......................... 540/145; 514/183, 514/185, 410

[56] References Cited

U.S. PATENT DOCUMENTS 5,726,169  3/1998  Scherz et al. .......................... 514/185

FOREIGN PATENT DOCUMENTS 1083185  4/1986  Japan .
1189284  8/1986  Japan .

*Primary Examiner*—Richard L. Raymond
*Assistant Examiner*—Pavanaram K Sripada
*Attorney, Agent, or Firm*—Greenlee, Winner and Sullivan, P.C.

[57] ABSTRACT

The present disclosure provides novel non-iron metalloporphyrins, especially those porphyrin complexes containing gallium or indium as the metal ion, and antibacterial compositions comprising artificial metalloporphyrins (such as protoporphyrin IX) completed with a metal ion selected from metal ions including, but not limited to, gadolinium, ruthenium copper, gallium, indium and manganese, and methods for inhibiting or killing bacteria and other microorganisms and for treating infections caused by microorganisms using the artificial metalloporphyrin of the present invention.

20 Claims, 3 Drawing Sheets

NON-IRON METALLOPORPHYRINS AND METHODS OF USE

CROSS-REFERENCE TO RELATED APPLICATIONS

This application claims priority from U.S. Provisional Application No. 60/035,079 filed Jan. 9, 1997, now abandoned.

ACKNOWLEDGEMENT OF FEDERAL RESEARCH SUPPORT not applicable

BACKGROUND OF THE INVENTION

The field of this invention is the area of antimicrobial agents and methods of treating infections and/or inhibiting microbial growth. Specifically, the present invention relates to inhibition of microbial growth and treating infections, especially those cause by pathogenic bacteria, with artificial metalloporphyrin.

The high incidence of microbial resistance to multiple antibiotics has seriously complicated treatment of infections of both outpatients and patients who have acquired hospital-associated infections. This rise in resistance to multiple antibiotics has made many otherwise very potent and inexpensive antibiotics almost obsolete [Cohen, M. L. (1992) Science, 257, 1050–1055; Neu, H. C. (1992) Science 257, 1064–1073]. Patients infected by multiply resistant bacteria have more severe clinical courses and require prolonged hospital treatments. Costs associated with these hospital acquired infections with resistant bacteria have been estimated to cost between $4 million and $30 billion per year in the United States alone [Haley, R. W. (1986) Managing Hospital Infection Control for Cost Effectiveness, Chicago, Ill., American Hospital Publishing]. Recent emergence of strains of enterococci which are resistant to all available antibiotics and chemotherapeutic agents is a clear reminder that, despite intensive research and production of new antibiotics, there is a real danger that the epidemic of multiple antibiotic resistance might not be stopped [Spera and Farber (1992) J.A.M.A. 268, 2563–2564]. Respiratory infections are a particularly serious problem due to their high incidence and alarmingly high mortality rates. Approximately 300,000 nosocomial lower respiratory infections occur each year in the United States, with mortality rates ranging between 20% and 50% [Pennington, J. E. in Harrison's Principles of Internal Medicine, 13th edition, K. I. Isselbacher et al., eds.].

The development of new antibiotics is a very costly endeavor with which, together with the lengthy process to obtain regulatory approval, is causing at least some pharmaceutical companies to abandon work in this area [Reich, M. R. (1987) Health Pol. 8,39–57; Slater, A. J. (1989) Trans. Royal Soc. Trop. Med. Hyg. 83, 45–48]. Thus, there is an urgent need in the art for the identification of new bacterial targets for antibiotic action and for the discovery of new antibacterial compounds that will foil bacterial resistance mechanisms.

SUMMARY OF THE INVENTION

An object of the present invention is to provide artificial metalloporphyrins with antimicrobial activity. Preferred porphyrin structures are given in Formula I (91–99) and Formula II (100–118). The metal ion components of the artificial metalloporphyrin of the present invention can include, without limitation, gadolinium, gallium, indium, manganese and ruthenium. Particularly preferred metalloporphyrin of the present invention include protoporphyrin IX derivatives with gallium (+3), indium (+3) and manganese (+2). Preferred protoporphyrin derivatives are those which do not have bulky substituents on the ring structure.

Within the scope of the present invention are methods for treatment of infection in an animal, including a human, from infection and disease and/or other pathology caused at least in part by bacterial, protozoan and certain fungal pathogens. Sensitive bacteria include Gram-positive organisms including, but not limited to, *Streptococcus pyogenes, Staphylococcus aureus, Bacillus subtilis;* Gram-negative bacteria including, but not limited to, Enterobacter spp., Klebsiella spp., Proteus spp., Yersinia spp., Neisseria spp, Bacteroides, Klebsiella spp., Citrobacter spp., *Vibrio cholerae, Heliobacter pyloris,* and *Escherichia coli;* acid-fast bacteria including, but not limited to, *Mycobacterium smegmatis, Mycobacterium tuberculosis, Mycobacterium avium* and *Mycobacterium bovis;* and fungi and yeasts including, but not limited to, *Saccharomyces cerevisiae,* Candida spp. and Cryptococcus spp.

Also within the scope of the present invention are compositions and methods for inhibiting microbial growth and/or killing bacteria, in infections, on surfaces, and in cosmetic, pharmaceutical and/or other preparations where bacterial contamination is advantageously minimized, such as contact lens solutions, using amounts of at least one metalloporphyrin effective for the inhibition of growth of at least one target bacterium, fungus or yeast. Growth inhibition and/or killing of microorganisms is not dependent on light. Microorganisms whose growth is inhibited (or are killed) are generally those which have heme uptake systems. Gram-positive bacteria, gram-negative bacteria and acid-fast bacteria are inhibited. The growth of fungi, including yeasts, is also inhibited by the non-iron metalloporphyrins of the present invention. Non-iron metalloporphyrins effective in the methods and compositions of the present invention include protoporphyrin IX containing gallium, gadolinium, indium, ruthenium, manganese, zinc, magnesium and chromium ions, desirably gallium, indium or manganese.

DETAILED DESCRIPTION OF THE INVENTION

Figure 1:
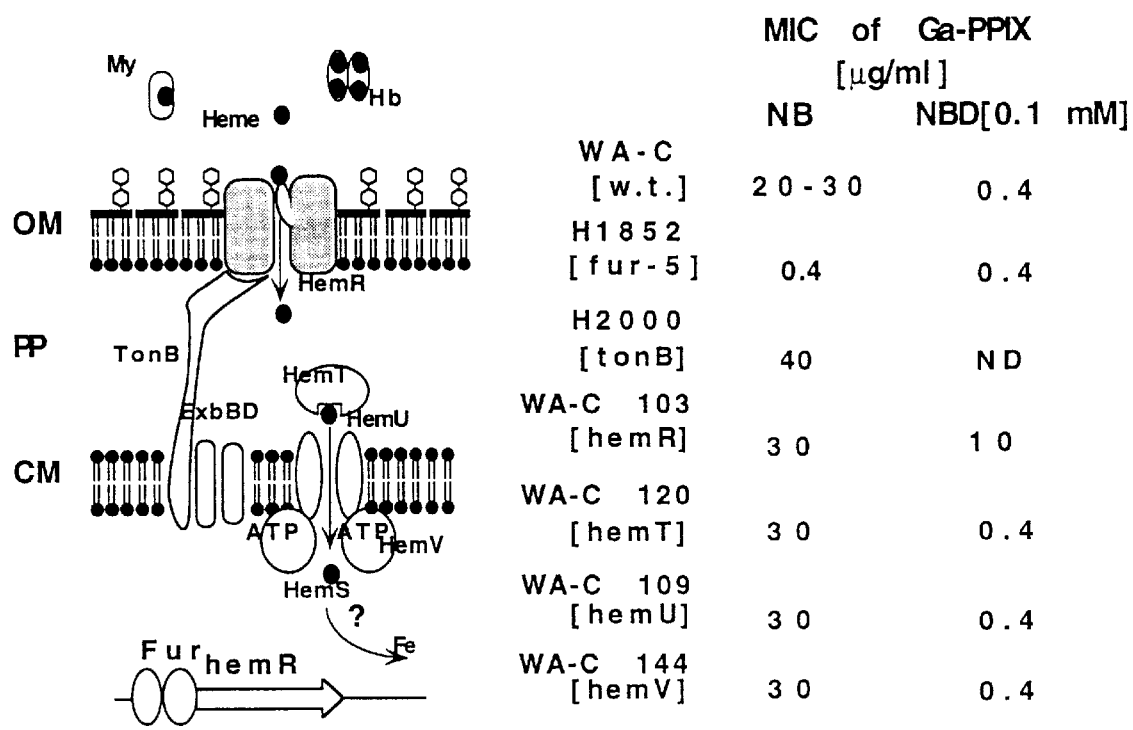
FIG. 1 provides MIC data for the activity of Ga-PPIX against *Y. enterocolitica* strains having mutations in components of the Hb/heme acquisition system [for discussion of mutants, see, e.g., Stojiljkovic and Hantke (1992, 1994); Koebnik et al. (1993) Mol. Microbiol. 237, 152]. The schematic representation of heme uptake pathway in *Y. enterocolitica* is as proposed by Stojiljkovic and Hantke (1992, 1994). ND=not done; NB=Nutrient Broth; NBD= Nutrient broth+0.1 mM dipyridyl; OM=outer membrane; PP=periplasm; CM=cytoplasmic membrane; MY=myoglobin; Hb=hemoglobin; w.t.=wild type.

Almost all pathogenic microorganisms utilize heme and hemoglobin as iron sources, and the utilization of heme-containing compounds is an important virulence determinant in a wide variety of microorganisms [Tai et al. (1993) Infect. Immun. 61, 5401 –5405; Cope et al. (1995) J. Bacteriol. 177, 2644–2653; Cornelissen-Nau and Sparling (1994) Mol. Microbiol. 14, 843–851; Genco et al. (1995) Infect. Immun. 63, 2359–2466; Jarosik et al. (1994) Infect. Immun. 62, 2470–2477; Weinberg, D. (1984) Physiological. Rev. 64, 65–102; Worst et al. (1995) Infect. Immun. 63, 4161–4165; Sompolinsky et al. (1978) Int. J. Syst. Bacteriol. 28, 67–75; Stojiljkovic et al. (1995) Mol. Microbiol. 15, 531–542] because iron is an essential element for growth in host body fluids and tissues. All heme/hemoglobin utilization systems in microorganisms have had to evolve in a way which solves the following problems: how to bind a heme-containing compound; how to release the heme from the compound or complex containing it; and how to transport the heme into the cell's interior. Heme and hemoglobin systems characterized to date appear to have evolved in a way that the solutions to the aforementioned problems have been very similar in a wide variety of bacteria which can use heme and/or hemoglobin as an iron source. Identification and partial characterization of heme and Hb binding proteins from the outer membranes of *Serratia marcescens* [Letoffe et al. (1994) Proc. Natl. Acad. Sci. USA 91, 9876–9880], *Neisseria gonorrhoeae* and *Neisseria meningitidis* [Stojiljkovic et al. (1995) supra; Letoffe et al. (1994) supra; Lewis and Dyer (1995) J. Bacteriol. 177, 1299–1306; Lee, B. C. (1991) J. Med. Microbiol. 36, 121–127; Stojiljkovic et al. (1996) J. Bacteriol. 178, 4670–4676], *Hemophilus ducreyi* [Elkins, C. (1994) Infect. Immun. 63, 1241–1245], *Helicobacter pylori* [Worst et al. (1995) supra], *Vibrio cholerae* [Henderson and Payne (1994) J. Bacteriol. 176, 3269–3277; Henderson and Payne (1993) Mol. Microbiol. 7, 461–469], *Porphyromonas gingivalis* [Genco et al. (1994) supra; Bramanti and Holt (1993) J. Bacteriol. 175, 7413–7420], *Plesiomonas shigelloides* [Panagiotis et al. (1991) Infect. Immun. 59, 2706–2711], *Bacteroides fragilis* [Otto et al. (1992) Crit. Rev. Microbiol. 18, 217–233], *Yersinia pestis* and *Y. enterocolitica* [Perry and Brubaker (1979) J. Bacteriol. 137, 1290–1298; Stojiljkovic and Hantke (1992) EMBO J. 11, 4359–4367; Stojiljkovic and Hantke (1994) Mol. Microbiol. 13, 719–732], *Hemophilus influenzae* [Cope et al. (1995) supra; Jarosik et al. (1994) supra; Cope et al. (1994) Mol. Microbiol. 13, 863–873], *Legionella pneumophila* [O'Connell et al. (1996) Infect. Immun. 64, 842–848], *Shigella dysenteriae* [Mills and Payne (1995) J. Bacteriol. 177, 3004–2009], *Escherichia coli* [Law and Kelly (1995) Infect. Immun. 63, 700–702] and *Aeromonas* spp. [Massad et al. (1991) J. Gen. Microbiol. 137, 237–241] showed that all heme-utilizing bacteria possess heme-specific outer membrane receptors.

Heme uptake systems are also widespread among Gram-positive bacteria. *Bacillus subtilis* [Hannson et al. (1993) J. Bacteriol. 173, 2590–2599], *Staphylococcus aureus* [Kafala and Sasarman (1994) Can. J. Microbiol. 40, 651–657], *Streptococcus pneumoniae* [Tai et al. (1993) supra], *Streptococcus pyogenes* and a pathogenic mycobacterium, *Mycobacterium haemophilum* [Sompolinsky et al. (1978) supra] are all proficient in the active transport of heme and its utilization. These systems are maximally expressed in the iron-limiting conditions of the human host fluids and tissues [Whitby et al. (1997) Infect. Immun. 65, 4696]. Heme uptake mechanisms of bacterial pathogens thus present an ideal site for targeted drug delivery. Protozoan pathogens sensitive to the metalloporphyrin of the present invention include *Leishmania donovani* and *Plasmodium falciparum*.

To exploit these systems for antibacterial therapy, the present inventors have discovered a class of chemical compounds with very strong and antibacterial activity, namely the "artificial" (non-iron) metalloporphyrin (MPs). Structures are given in Formula I (91–99) and Formula II (100–110) (Scheme I).

An important advantage of MPs is that they enter the bacterial interior through high-affinity heme transport systems and are not affected by the barrier functions of bacterial membranes. This minimizes the impact of resistance to MPs because resistant mutants are less fit to survive in body fluids and tissues due to their inability to utilize heme. MPs are the first antimicrobial compounds that target cytochrome function and/or assembly, and they are therefore not affected by antibiotic resistance mechanisms present in bacteria. MPs are the basis of new antifungal, antiparasitic and anticancer drugs because modification of the porphyrin periphery confers qualitatively a new spectrum of activities to MPs.

Certain artificial (non-iron) metalloporphyrins (MPs) are active against Gram-negative and Gram-positive bacteria and acid-fast bacilli as well (Tables 1–5). Some MPs are also growth-inhibitory against yeasts, indicating their potential usefulness in the treatment of yeast infections, due, for example, to Candida species (see, e.g., Table 8), and other mycoses, including but not limited to those caused by as Trichophyton, Epidermophyton, Histoplasma, Aspergillus, Cryptococcus, and the like. Experimental evidence indicates that MPs gain access to the bacterial cell cytoplasm via the heme-specific uptake pathways.

Gallium derivatives of modified porphyrins (uroporpyrin I, uroporphyrin III, coproporphyrin III and chorin $e_6$), although mainly inactive against bacteria with the exception of Ga-chlorin $e_6$, inhibited growth of the yeast *Saccharomyces cerevisiae* in vitro. These modified porphyrins also inhibit the growth of *Candida albicans, Candida krusei* and *Candida pilosus* (Table 8, Ga-uroporphyrin I data). Although the MICs of these modified MPs against yeasts were up to 10-fold higher than the MIC of the anitifungal drug fluconasol, fluconasol-resistant yeast isolates were not also resistant to MPs. These MPs were also toxic to mammalian cells in culture, with that cytotoxicity observed at concentrations of 50 to 100 micrograms/mL.

Utilization of heme-containing compounds is an established virulence characteristic of a wide variety of Gram-negative and Gram-positive bacterial pathogens. However, rare bacterial mutants that fail to express heme uptake systems will become resistant, but these mutants will simultaneously become less virulent due to their reduced ability to scavenge iron [Tai et al. (1993) supra; Stojiljkovic et al. (1996) supra]. This minimizes the impact of resistance to MPs because the resistant mutants will be at a disadvantage for survival in body fluids and tissues. Moreover, bacterial heme uptake systems are maximally expressed under the iron-limiting conditions of an infection, thus, the antibacterial activity of the MPs is potentiated in vivo by the body's defense mechanisms.

In the study of the HemR-dependent heme uptake of *Y. enterocolitica*, we discovered that certain non-iron metalloporphyrin are toxic to bacteria that express heme uptake systems. Manganese protoporphyrin IX (Mn-PPIX), but not Sn-PPIX and Mn-meso-tetra-4-sulfonatophenyl porphine, inhibited growth of *E. coli* EB53 (hemPR$^+$) on Nutrient Broth Dipyridyl plates (NBD 0.1 mM). Mn-PPIX inhibited growth of heme-utilizing bacteria in the absence of Hb/heme, indicating that this compound does not affect heme accumulation or heme/Hb utilization.

In order to determine which metals confer antibacterial activity when inserted into protoporphyrin IX, eighteen different MPs were tested for inhibition of growth of heme-utilizing Gram-negative (*Y. enterocolitica* 0:8 *fur* mutant) and Gram-positive bacteria (MRSA (methicillin resistant) *S. aureus*), and acid-fast bacteria (*M. smegmatis* LR222). The *Y. enterocolitica fur* mutant was used because it expresses the heme uptake pathway constitutively. Ga-, Gd-, In- and Pt-PPIX were synthesized using the well known protocols [Coutsolelos and Guilard (1983) J. Organometal. Chem. Polyhedron 253, 273; Macquet and Theophanides (1973) Can. J. Chem. 51, 219]. Only Ga-, In- and Mn PPIX were inhibitory for *Y. enterocolitica* and *M. smegmatis*. In addition to Ga-, In- and Mn-PPIX, Zn- and Ru-PPIX showed some activity against *S. aureus* (Tables 1–4). All other MPs tested had 20- to 100-fold higher MIC values (Tables 1–4).

Only bacteria expressing heme/Hb utilization pathway(s) are sensitive to MPs. Indeed, the hemR mutant of *Y. enterocolitica*, unable to use heme as an iron source, is resistant to relatively high concentrations of Ga-PPIX (Table 6). The inability of the TonB mutant of *Y. enterocolitica* to grow in low-iron conditions precluded the determination of the MIC of Ga-PPIX for this mutant. Ga-PPIX inhibition assays done with a *E. coli* TonB mutant overexpressing HemR from a multicopy plasmid indicated that the TonB activity is necessary for Ga-IX inhibition. These experiments established that Ga-PPIX enters the bacterial periplasm through the TonB-dependent *Y. enterocolitica* HemR heme transporter. The cytoplasmic membrane heme uptake system, consisting of the HemT, HemU, and HemV proteins, was not required for Ga-PPIX sensitivity because hemT, hemU and hemV mutants were fully sensitive to Ga-PPIX. Thus, Ga-PPIX targets metabolic pathway(s) in the bacterial periplasm, or the transport of MPs across the cytoplasmic membrane occurs through more than one system.

MPs are active against Gram-negative bacteria grown in low-iron media (i.e., Nutrient broth+0.1 mM dipyridyl) which induce maximal expression of outer membrane heme transporters (FIG. 1). Accordingly, the *Y. enterocolitica fur* mutant which constitutively expresses HemR was fully sensitive to MPs in iron-rich media (FIG. 1). Iron restriction, however, played only a minor role in sensitizing *S. aureus* and *M. smegmatis* to MPs. While the MIC of Ga-PPIX against *Y. enterocolitica* wild type strains differed 50- to 100-fold depending on the growth conditions (i.e., low iron versus high iron) (FIG. 1), the MICs of Ga-PPIX for *S. aureus* and *M. smegmatis* were only 2-fold lower when the strains were grown in low iron media (NBD with 0.1 mM dipyridyl for *S. aureus* and LB+0.2 mM Desferal for *M. smegmatis*).

MICs of Ga- and In-PPIX against several clinical and laboratory isolates are shown in Tables 1, 4 and 5. Among the bacteria tested, only *S. pyogenes* was resistant to both Ga-PPIX and Mn-PPIX. Although MP concentrations as low as 0.2 µg/ml strongly inhibited the growth of *S. aureus,* only concentrations above 1 µg/ml completely abolished residual growth (see also FIG. 2A). The MIC of Ga-PPIX against *S. aureus* determined in Muller-Hinton broth did not differ significantly from the value obtained in NB broth.

Figure 2A:
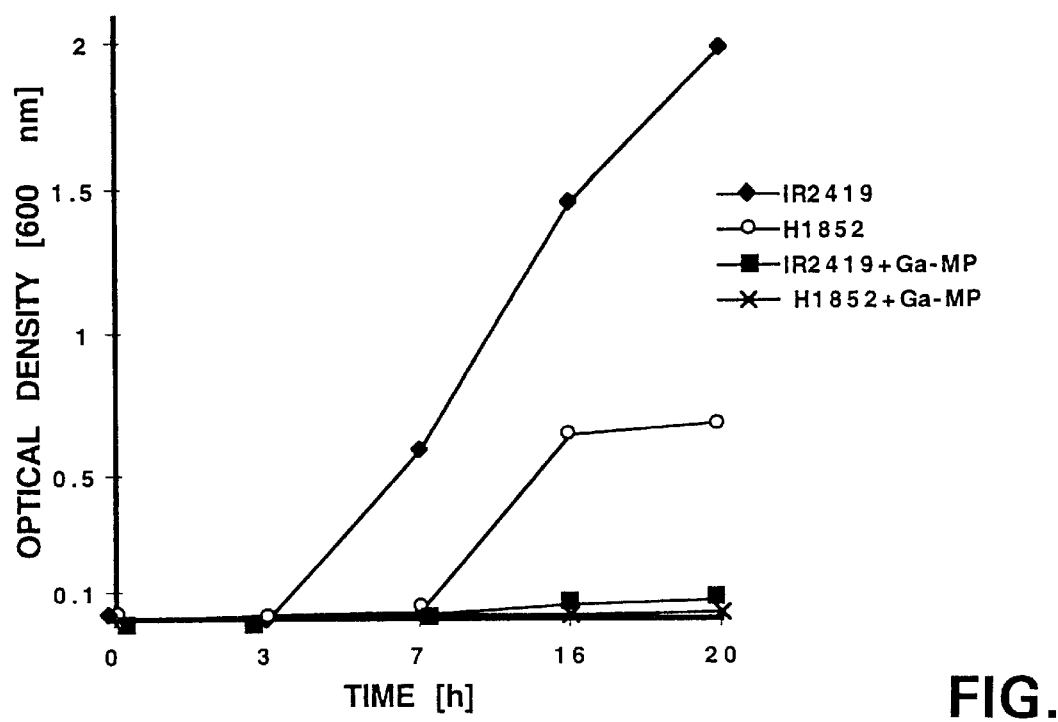
FIG. 2A illustrates growth kinetics for *Y. enterocolitica fur* (H1852) and methicillin resistant *S. aureus* IR2419 in NB medium containing 1 μg/ml of Ga-PPIX.
Figure 2B:
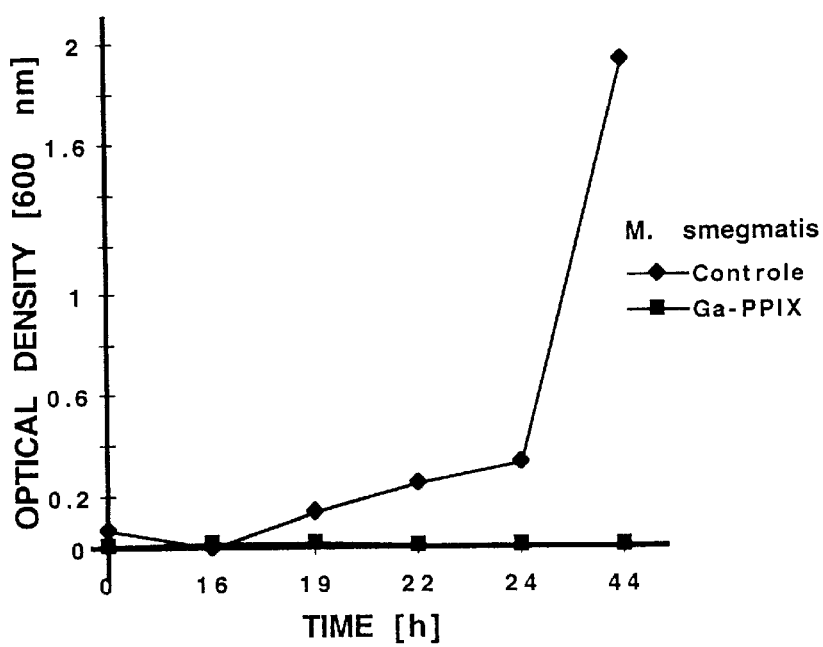
FIG. 2B illustrates growth kinetics of *M. smegmatis* LR222 in LB+Tween 80 medium containing 1 μg/ml of Ga-PPIX. Bacteria were inoculated to approximately $3 \times 10^5$ CFU and incubated at 37° C. with vigorous aeration from 20 to 44 hours.
Figure 3:
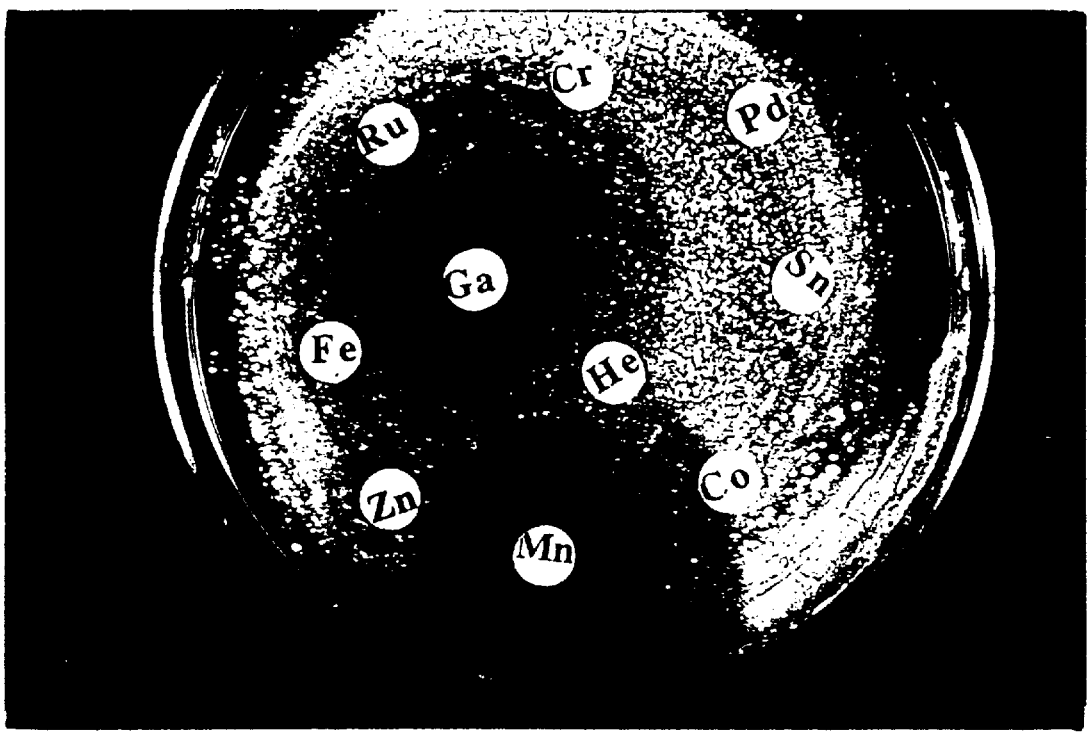
FIG. 3 is a photograph showing the inhibition of growth of *Mycobacterium bovis* by various MPs. Approximately $10^6$ bacteria were plated onto Middlebrook 7H11 agar plates and sterile filter paper discs each containing 50 micrograms of MP were placed on the surface of the plates. Ga=PPIX, Mn=MnPPIX, Zn=ZnPPIX, He=FePPIX, Fe=meso-tetra-4-sulfonatophenyl porphine, Ru=RuPPIX, Cr=CrPPIX, Pd=PdPPIX, Co=CoPPIX, Sn=SnPPIX.

The kinetics of bacterial growth in the presence of 1 µg/ml of Ga-PPIX are shown on FIGS. 2A and 2B. At this concentration, Ga-PPIX completely prevented growth of *Y. enterocolitica* and *M. smegmatis,* which was expected from MICs of Ga-PPIX for these bacteria (see also Table 2). Concentrations of Ga-PPIX that were below the MIC value inhibited growth of *S. aureus* in the first 20 hours of growth (FIG. 2A). The residual growth was not due to the emergence of MP-resistant clones in the culture because bacteria isolated from the culture were still sensitive to MPs. Without wishing to be bound by any particular theory, it is believed that the ability of *S. aureus* to overcome the antibacterial activity of MPs is due to a metalloporphyrin-degrading activity.

The antibacterial activities of MPs against a large number of clinical isolates, some of which were resistant to several antibiotics, were assessed by a disc diffusion assay. Briefly, inhibition zones obtained by placing discs containing 50 µg of MPs onto plates inoculated with $10^6$ to $10^7$ iron-restricted bacteria were recorded and compared with inhibition zones obtained with reference to Ga-PPIX-sensitive bacteria (Tables 1 and 2). Clinical isolates with similar or larger inhibition zones than those obtained with Ga-PPIX-sensitive bacteria were considered potentially sensitive to the particular MP. Inhibition of growth of *M. bovis* (BCG) by different MPs obtained by this method is shown in Tables 2 and 5. Ga-PPIX and Mn-PPIX were the only compounds among 17 different MPs tested (see Table 2) that produced inhibition zones larger or equal 20 mm in diameter on lawns of strains of *Citrobacter freundii* (4/4), *Proteus mirabilis* (2/2), *Escherichia coli* (16/18), *Serratia marcescens* (2/3), *Klebsiella pneumoniae* (9/13), *Klebsiella oxytoca* (1/1), *Flavobacterium meningosepticum* (1/1), *Enterobacter aerogenes* (1/1), *Staphylococcus aureus* (9/9), *Staphylococcus carnosus* (1/1) and *Staphylococcus xylolus* (1/1). Isolates of *Pseudomonas aeruginosa* (0/7) and *Enteroccocus faecalis* (0/9) were, however, resistant to all MPs tested.

MICs of porphyrins that do not contain metal ions were determined to learn whether these compounds possess antibacterial activity. Protoporphyrin IX, porphine and chlorin $e_6$ without Ga ions had very large MICs for all tested bacteria (Tables 10 and 11). Insertion of Ga into protoporphyrin IX reduced MICs by 25- to 100-fold for all tested bacteria (Tables 2 and 10). Introduction of Ga ion into porphine had no effect on the MIC, while the Ga-chlorin $e_6$ derivative was active against *S. aureus* and *M. smegmatis* but significantly less active against *Y. enterocolitica*. Mesoporphyrin IX and, to a lesser degree, octaethylporphine and uroporphyrin I without any metal ion, had some activity against a *Y. enterocolitica fur* mutant (MIC of 2.5, 5 and 10 µg/ml, respectively) (Table 10). Bacterial sensitivity to octaethylporphine and uroporphyrin I did not require expression of HemR since MIC of the hemR mutant was almost identical to MIC of the hemR$^+$ bacteria (Table 10). Comparison of the MICs for the *Y. enterolitica hemR* and *fur* mutants indicates the level of the HemR-dependent inhibition. Octaethylporphine exhibited limited activity against *S. aureus* and *M. smegmatis* while mesoporphyrin IX and uroporphyrin I were largely inactive against these bacteria.

A very large alteration of porphyrin structure, for example, that in Mn-meso-tetra-4-sulfonatophenyl porphine, destroyed the antibacterial activity of MPs. Curiously, Ga-uroporphyrin I, Ga-uroporphyrin III, and Ga-coproporphyrin I, although seriously limited in their antibacterial activities, were able to inhibit growth of yeast. However, these MPs were also cytotoxic for eukaryotic cell cultures at concentrations of 50 to 100 µg/ml. Ga-chlorin $e_6$ inhibited growth of bacteria and, to a lesser extent, yeast, and it was also cytotoxic to human cells in culture.

Bacterial mutants in heme uptake systems are fully viable in vitro (i.e., in microbiological media) because a vast majority of bacteria synthesize heme and because most microbiological media provide sufficient non-heme iron [Stojiljkovic and Hantkce (1992) supra]. Accordingly, incubation of Gram-negative bacteria in the presence of Ga-PPIX gave rise to spontaneous resistant colonies that had lost the ability to use heme. However, the same approach did not produce spontaneous resistant mutants of *S. aureus* and *M. smegmatis*. If MPs use heme transporters to get to their cytoplasmic targets, spontaneous-resistant mutants should have been isolated since heme transport is not an essential function in these bacteria. Without wishing to be bound by theory, it is postulated that these data indicate that the MP targets are surface-exposed in *S. aureus* and *M. smegmatis*, and the MPs do not require heme transporters to reach their targets.

MPs enter Gram-negative bacteria through high-affinity heme uptake receptors (FIG. 1). The ability of heme to compete with the antibacterial activity of Ga-PPIX against *Y. enterocolitica fur* mutant corroborated the role of HemR in MP transport (Table 11). Conversely, protoporphyrin IX was not able to antagonize antibacterial activity of Ga-PPIX (Table 11), most likely because it cannot bind to and be transported by the HemR receptor. Ten- to 100-fold molar excess of heme did not antagonize antibacterial activity of Ga-PPIX against *M. smegmatis* and *S. aureus* (Table 11). Surprisingly, a 20- and 100-fold excess of protoporphyrin IX antagonized Ga-PPIX antibacterial activity against *M. smegmatis*. Only 100-fold excess of protoporphyrin IX had some antagonizing effect on the Ga-PPIX-mediated activity against *S. aureus* (Table 11). The inability of heme to antagonize antibacterial activity of Ga-PPIX against *M. smegmatis* and *S. aureus* indicates that the transport of MPs through heme-specific channels is either not required for MP activity or there is more than one heme uptake pathway in these bacteria. Heme uptake systems of Gram-positive and acid-fast bacteria have not been characterized at the molecular level.

Due to the structural similarities to heme, MPs may inhibit some essential metabolic pathway in bacteria that uses heme as a cofactor. Two highly conserved metabolic functions in bacteria that use heme as a catalyst and/or regulator are respiration and heme biosynthesis [Gennis and Stewart (1996) in *Escherichia coli* and *Salmonella typhimurium*, second edition, F. C. Neidhardt et al. (eds.), ASM Press, Washington, C.C., pp. 217–261; Beale, S. I. ibid., pp. 731–748]. Both wild type *E. coli* K-12 (hemPR+) and a hemA heme biosynthesis mutant were fully sensitive to Ga-PPIX when grown in the presence of delta-aminolevulinic acid. This result indicated that MPs do not inhibit the key step in heme biosynthesis, formation of delta-aminolevulinic acid [Padmanaban et al. (1989) Trends. Biochem. Sci. 14, 492; Wang et al. (1997) J. Bacteriol. 179, 2907]. However, anaerobically grown *E. coli* K-12 (hemPR+) was fully resistant to the action of MPs, suggesting that these compounds target bacterial respiration. Alternatively, MPs may sensitize the bacteria to oxygen radicals normally produced during respiration.

*E. coli* cells express two main respiratory oxidases, cytochrome bd (maximally expressed under microaerophilic conditions) and cytochrome bo expressed under conditions of high aeration. Both oxidases contain noncovalently bound heme molecules which are essential for their function [Gennis and Stewart (1996) supra]. To determine whether MPs target cytochrome assembly/function, *E. coli* mutants in cytochrome bd, cytochrome bo, NADH dehydrogenase II, and anaerobically expressed cytochrome c synthesis operon (ccmABCDEFGH) were tested for sensitivity/resistance to Ga-PPIX [Calhoun et al. (1993) J. Bacteriol. 175, 3032; Thöny-Meyer et al. (1995) J. Bacteriol. 177, 4321]. Since *E. coli* K-12 does not transport heme across the outer membrane, all K-12 strains were transformed with a plasmid from which the *Y. enterocolitica hemR* gene is expressed [Stojiljkovic and Hantke (1992) supra].

All strains transformed with the HemR-expressing plasmid were sensitive to less than 0.5 μg/ml of Ga-PPIX when grown with slight iron restriction (0.05 mM dipyridyl) (Table 7). However, only cytochrome cd and cyo single mutants were still sensitive to Ga-PPIX when grown without an iron chelator. All other mutants used in the study had 50-fold higher MIC values when grown under iron-sufficient growth conditions (Table 7).

To test for toxicity of MPs for mammalian cells, semiconfluent monolayers of four cell lines (MRC-5 primary human fibroblasts, Vero cells, MDCK cells and CaCO-2 cells) were incubated for 24 to 48 hours in the presence of 5, 25, 50, 250 and 400 μg/ml of Ga-PPIX dissolved in 0.02 M NaOH. No detachment or rounding of cells was noticed in any of the monolayers. Preliminary toxicity testing on animals showed that a single intraperitoneal dose of 25 mg/kg of Ga-PPIX does not cause any peracute or acute effect on the health and behavior of mice.

Sensitivity to MPs correlated with the ability of microorganisms to use heme (Fe lane, Table 6). Manganese, gallium and indium protoporphyrins have the widest antibacterial spectrum of activity (Table 2). Clinical strains of *C. freundii* (4/4), *P. mirabilis* (2/2), *E. coli* (16/18), *S. marcescens* (2/3), *K. pneumoniae* (9/13) and *S. aureus* (9/9) were tested and were almost universally sensitive to Gallium protoporphyrin. Preliminary experiments indicate that pathogenic *Mycobacterium tuberculosis* and *M. avium* are sensitive to indium and gallium protoporphyrins. *Ps. aeruginosa* (0/7) and *Enterococcus faecalis* (0/9) were not sensitive to any MP. Minimal inhibitory concentrations (MIC) of gallium-protoporphyrins and manganese-protoporphyrins against various bacteria were determined (Table 5). The gallium-protoporphyrin showed the widest spectrum and the highest level of antibacterial activity. When iron-rich medium was used, MICs for the majority of the bacteria were larger than the MICs for the same microorganisms grown under conditions of iron limitation, indicating that iron-restriction is necessary for optimal antibacterial effects. Such iron-limited conditions exist in the animal and human body tissues and fluid [Weinberg (1984) supra; Litwin and Calderwood (1993) Clin. Microbiol. Rev. 6, 137–149].

The *Y. enterocolitica* mutant (hemR) defective in heme transport across the outer membrane and other bacterial strains that are unable to use heme were fully resistant to MPs (Table 6). However, the *Y. enterocolitica* mutants defective in the transport of heme across the cytoplasmic membrane (hemU, hemV) were fully sensitive to the action of MPs. This finding suggests that the target of MPs is in the periplasmic space of Gram-negative cells.

Gallium, indium and manganese porphyrin derivatives are inhibitory to various microorganisms. Ga-IX is the MP tested which exhibits the widest spectrum of antibacterial activity. Typically, the MIC (minimal inhibitory concentration) was in the range of 0.1 to 1.0 μg/mL. Gallium protoporphyrin is a relatively safe compound for animals in that gallium salts and certain MPs have been used without serious side effects in the diagnosis and treatment of human diseases. An important advantage of MPs is that they enter bacterial cells through high-affinity heme uptake systems and are therefore not affected by barrier functions in bacterial membranes. Bacterial heme uptake systems are maximally expressed under iron-limiting condition of the host, which would tend to potentiate the antibacterial activity of these MPs in vivo. Utilization of heme as a source of iron in the host is an important virulence mechanism for many bacterial pathogens. This minimizes the impact of resistance to MPs because resistant mutants are less fit to survive in body fluids and tissues due to their inability to synthesize heme. Gallium (+3) hematoporphyrin IX, which has hydroxymethyl rather than vinyl groups (Formula I, 92), was active against all microorganisms challenged. Manganese (+2)-meso-tetra-4-sulfonatophenyl porphine was inactive.

Some porphyrin derivatives are already used in the treatment of certain noninfectious diseases in humans. Hemin is used in the treatment of various porphyria and in lead poisoning; heme arginate is used in the treatment of sideroblastic anemias; tin-protoporphyrin IX is used to treat biliary cirrhosis, neonatal jaundice, psoriasis and Gilbert's syndrome [Cannon, J. B. (1993) J. Pharm. Sci. 83, 435–446]. Gallium nitrate is frequently used in the treatment of clinical syndromes including hypercalcemia of malignancy, Paget's disease of bone, parathyroid carcinoma and osteolytic bone metastases [Hughes and Hansen (1992) Ann. Pharmacotherapy 26, 354–262; Marcus, R. (1994) in The Pharmacological Basis of Therapeutics. IX edition, J. G. Hardmann et al., eds., McGraw-Hill]. Reversible nephrotoxicity is the only major complication which has been observed following treatment with gallium nitrate, and it occurs in those patients in whom kidney function is already compromised and at high dosages [Hughes and Hansen (1992) supra; Marcus (1996) supra]. Similar toxicity occurs in patients treated with aminoglycosides, antibiotics which are routinely used in the treatment of a wide variety of bacterial infection [Marcus (1996) supra]. These reports suggest that the gallium protoporphyrin would not be expected to cause major side affects in animals or in human patients.

Neither the mechanism of action nor the biochemical target for MPs is currently known. The exceptionally (and surprisingly) wide spectrum of microbial action indicates that MPs affects a very conserved and likely essential metabolic function(s) in bacteria.

Pharmaceutical compositions contain a therapeutically effective amount of an artificial metalloporphyrin. A therapeutically effective amount of an MP can be readily determined according to methods known in the art. Pharmaceutical compositions are formulated to contain the therapeutically effective amount of an MP and a pharmaceutically acceptable carrier appropriate for the route of administration (topical, gingival, intravenous, aerosol, local injection) as known to the art. For agricultural use, the composition comprises a therapeutically effective amount of an MP and an agriculturally acceptable carrier suitable for the organism (e.g., plant) to be treated. The skilled artisan can readily determine a therapeutically effective amount against a target bacterial (or other microbial) strain, for example, based on the MIC or MBC using the methods disclosed herein and the teachings of the art.

Therapeutic compositions may be administered by topical, dental rinse, aerosol or intravenous application, or by local injection for the control or prevention of infection, by any means known to the art.

Antibacterial pharmaceutical compositions, as defined herein, comprise a pharmaceutically acceptable carrier and one or more MPs of the present invention. Such antimicrobial pharmaceutical compositions may be formulated in ways, as understood in the art, for use for topical application, for gingival application (for gingivitis or periodontal disease) or for local or systemic injection. For use in the treatment or prevention of gingivitis, the peptides of the present invention can be incorporated in effective amounts in a dental rinse for application to the buccal area, or they may be incorporated in other suitable compositions for topical application. Similarly, where killing or inhibition of microbial growth is desired in compositions, an amount of MP(s) effective for killing of inhibition of microbial growth is readily determined by the ordinary skilled artisan. The MPs of the present invention can comprise from 0.001% to 50% by weight of the foregoing compositions. The choice of the MP will be made with consideration of immunogenicity and toxicity to the infected host, effective dose, and the sensitivity of the target microbe to the MP, as wellunderstood in the art.

For inhibition of microbial growth, at least one MP of the present invention is present in the solution or other composition to be preserved or protected at a concentration equal to or greater than the MIC or MBC for at least one target microorganism. The target organism is selected accordingly to the particular composition and the environment in which that composition is used, as readily apparent to the relevant skilled artisan. It will be further apparent that toxicity to nonmicrobial cells and the intended usage of the preserved composition also affect MP choice and concentration. For example, a contact lens solution would not comprise cytotoxic amounts of an MP if that soloution were to come in contact with the eye.

In general, concentrations of a MP used for inhibition in a solution are in the range from about 0.05 to about 1000 $\mu$g/ml, or about 0.1 to about 100 $\mu$g/ml, or in other compositions from about 0.05 to about 1000 $\mu$g/g, or from about 0.1 to about 100 $\mu$g/g, or from about 0.5 to about 50 $\mu$g/g. MPs are dissolved in an appropriate solvent, for example, from about 0.25 to about 200 mM NaOH, and then the MP solution can be diluted or introduced into a solution or other composition in which microbial growth is to be inhibited. If MPs are to be incorporated into a therapeutic composition, the initial MP solution is combined with a pharmacologically acceptable carrier or diluent, preferably sterile, to provide a pharmaceutical composition. The pharmaceutical composition will contain the MP at a concentration from about 0.01 to about 50 mg/ml.

All references cited herein are hereby incorporated by reference in their entirety. Abbreviations and nomenclature, where employed, are deemed standard in the field and commonly used in professional journals such as those cited herein.

The foregoing discussion and the following examples illustrate but are not intended to limit the invention. The skilled artisan will understand that alternative methods may be used to implement the invention.

EXAMPLES

Example 1

Assessment of Antibacterial Activity of MPs

Bacteria, including multidrug-resistant clinical isolates, are tested for susceptibility to MPs, specifically gallium, indium and manganese derivatives. The effects of growth conditions, including anaerobiosis, aerobiosis, low pH, presence of serum, blood, hemoglobin and heme, are also tested. In general, growth under low (restrictive) iron conditions leads to increased susceptibility where the strain is susceptible.

Bacterial strains used in this study are listed in Table 9. *Y. enterocolitica* and *S. aureus* were routinely cultured in Nutrient Broth with salt (8 g of Nutrient broth, 5 g NaCl per liter). *M. smegmatis* LR222 was cultured in Luria Broth with 0.5% Tween 80. *M. bovis* was grown in Middlebrook 7H9 medium with OACD supplements, Neisseriae were grown in GC medium with supplements; Listeriae were grown in LB; *B. subtilis* and *S. aureus* were grown in NB medium and *S. pyogenes* in Todd-Hewitt medium. When needed, iron restriction was accomplished by addition of 0.1 mM dipyridyl to Nutrient Broth or 0.2 mM Desferal (Ciba Geigy) to LB broth. Todd-Hewitt broth was used for cultivation of streptococci. Middlebrook-Conn medium with OACD supplements was used for growth of *M. bovis*. Clinical isolates were obtained from Dr. Richard Nolte, Clinical Microbiology Laboratory, Emory University Hospital, Atlanta, Ga. Chemicals were purchased from Sigma (St. Louis, Mo.), Aldrich Co. (Milwaukee, Wis.) and Porphyrin Products, Inc. (Logan, Utah).

For MIC determination with most bacteria, 1 mL of Nutrient Broth (Difco Laboratories, Detroit, Mich.) was inoculated with about $1 \times 10^5$ to $3 \times 10^5$ bacterial cells. The growth medium was supplemented with 0.1 mM 2,2'dipyridyl and varied concentrations of MP. Bacterial growth was recorded after overnight incubation at 37° C. For the growth of *M. smegmatis* LB medium containing 0.05% Tween 80 and 0.2 mM Desferal (Sigma Chemical Co., St. Louis, Mo.) was used. Middlebrook-Conn medium with OADC supplements (Difco Laboratories) was used for the growth of *M. bovis*. Todd-Hewitt broth was used for growth of *S. pyogenes*. *N. meningitidis* was grown in Brain Heart Infusion broth (Difco Laboratories). MIC values for ampicillin, vancomycin and chloramphenicol were not affected by the iron restriction medium conditions, indicating that neither iron restriction nor the 2,2'-dipyridyl affect bacterial viability.

Porphyrins and metalloporphyrin were dissolved in DMSO (dimethylsulfoxide), DMF (dimethylformamide) or 0.02 M NaOH at 5 mg/ml and stored in the dark. Bacteria were diluted to approximately $1-5 \times 10^5$ per ml in appropriate media (see above). Different amounts of porphyrins were added to diluted bacteria and incubated on a rotatory wheel at 37° C. for 20, 24 (*S. aureus*) or 48 (*M. smegmatis*) hours [Hindler et al. (1994) in Clinical and Pathogenic Microbiology, 2nd edition, Howard, B. J. et al. (Eds.), St. Louis, Mo., Mosby-Year Book, Inc., pp. 145–195]. Experiments were done using bacterial inocula from stationary cultures to limit the amount of iron accumulated in the bacterial cells. Bacterial cultures were incubated in the dark; addition of MPs to the culture was done in the presence of artificial light. All measurements were repeated at least three times (usually five to ten times).

Minimal bactericidal concentrations (MBCs) were determined essentially the same way as MICs except that the amount of killing with a particular concentration of porphyrin derivative was determined by plating on solid microbiological media (LB plates or LB+Tween 80). Media were solidified by the incorporation of 1.5% agar (Difco Laboratories). Concentrations of porphyrins that produced 99.9% reduction in bacterial counts were considered bactericidal [Hindler et al. (1994) supra]. Results of MIC and MBC experiments did not depend on the solvent in which MPs were dissolved.

For sensitivity testing on agar plates with about 50 μg in 10 μL sterile solution of MP applied to a sterile 6 mm diameter filter paper disk (Whatman, Clifton, N.J.) after the surface of the solid medium was inoculated with about $10^6$ to $10^7$ bacterial cells. Broth media were solidified with 1.5% agar (Difco Laboratories). Zones of inhibition were measured after 24 or 48 hours of incubation.

Example 2

Competition Experiments

In order to determine whether heme or protoporphyrin IX competes with the antibacterial activity of MPs, the abilities of *S. aureus* IR2419, *M. smegmatis* and *Y. enterocolitica* H1852 to grow in the presence of 1 μg of Ga-PPIX together with a 10- to 100-fold molar excess of heme and protoporphyrin IX excess were assessed. Briefly, 1 μg of Ga-IX was added to 1 ml of Nutrient Broth (LB+Tween 80 in the case of *M. smegmatis*) containing approximately $3 \times 10^5$ bacteria and 1 to 100 μg of heme or protoporphyrin IX. Control experiments with Ga-PPIX, heme and protoporphyrin IX were also carried out. The toxic effect of heme on *S. aureus* as described by Nitzan et al. (1987) FEMS Microbiol. Lett. 48, 401 was not observed in the present studies. The reasons for this discrepancy are not clear. However, the inventors used different bacterial strains and heme that had been dissolved in 20 mM NaOH instead of 0.5 M NaOH [Nitzan et al. 1987), supra].

Example 3

Isolation and Characterization of MP-resistant *E. coli*

To facilitate the understanding of the mechanism of resistance to MPs, spontaneous, transposon-induced and/or chemically induced resistant mutants of *E. coli* and *S. aureus* are isolated and characterized with respect to the ability to take up heme. *E. coli* mutants can transport heme but which are resistant to MPs are studied further. Without wishing to be bound by theory, these mutants are believed to be mutated in MP targets and not in the heme transport functions used to bring heme and related molecules into the bacterial cytoplasm (see Table 6). The mutated genes are mapped using a set of HFR mapping strains and fine mapped by transduction using an ordered library of *E. coli* Tn5 mutations [Low, B. K. (1987) in *Escherichia coli* and *Salmonella typhimurium:* Cellular and Molecular Biology, F. C. Neidhardt, ed., ASM Press, Washington, D.C, pp.1134–1137; Berg and Berg (1987) ibid., pp. 1071–1109]. An ordered *E. coli* cosmid library is used to clone and characterize the gene and/or genes that are affected in the MP phenotype [Birkenbihl and Vielmetter (1989) Nucl. Acids Res. 17, 5057–5069]. This allows the cloning of the gene which is responsible for the resistance phenotype. *E. coli* mutants which are resistant to MPs and which are also unable to use heme as an iron source are considered to be the result of a defect in the heme uptake system. The roles of *Y. enterocolitica* genes involved in the transport of heme and in the resistance to MPs have already been characterized.

Example 4

Synthesis and Characterization of Metalloporphyrin

The periodic table of metalloporphyrins which have been either synthesized in the laboratory and/or isolated from nature has been described [Smith, K. M. (1975) *Porphyrins and Metalloporphyrins,* Elsevier Scientific Publishing Company, Amsterdam; Dolphin, D. (1978) Academic Press, NY, both incorporated by reference]. The present inventors have identified three PPIX derivatives with significant antibacterial activity, i.e., those with gallium, indium and manganese.

Ga-PPIX, In-PPIX, Ga-OEP, Ga-MPIX, Ga-$C_{e6}$, Ga-POR, Ga-UPI, Ga-UP III, and Ga-COP I were synthesized essentially as described by Coutsolelos and Guilard (1983) J. Organometal. Chem. 253, 273. Gadolinium protoporphyrin IX was synthesized as described by Wong et al. (1974) J. Am. Chem. Soc. 96, 7149. Platinum protoporphyrin IX was synthesized as described by Macquet et al. (1977) Can. J. Chem. 51, 219. The reactions were monitored by absorption spectroscopy. Ga-PPIX was identified by mass and NMR spectroscopy. Indium (III) protoporphyrin IX chloride: UV-Vis $\lambda_{max}$ (nm) MeOH: 413, 546, 585. Gadolinium CIII protoporphyrin IX chloride: UV-Vis $\lambda_{max}$ (nm) AcOH: 398, 404, 538, 560. Gallium (III) protoporphyrin IX chloride: UV-Vis $\lambda_{max}$ (nm) MeOH: 409, 540, 579; Mass (M+-HCl) m/e 629.88 (calculated 629.38); $^1$H NMR (400 MHz, DMSO-$d_6$) 5 2.91 (2H, $CH_2COOH$); 3.37–4.52 (18H, $CH_2COOH+CH_2Ar+4CH_3$); 6.29 (2H, CH=$CH_2$); 6.52 (2H, CH=$CH_2$); 8.54 (1H, CH=$CH_2$); 8.59 (1H, CH=$CH_2$); 10.37–10.60 (4H, methine H's). Ga-OEP: UV-Vis $\lambda_{max}$ (nm) MeOH: 394, 396, 530, 568; Ga-MPIX: UV-Vis $\lambda_{max}$ (nm) MeOH: 397, 531, 568; Ga-Ce6: UV-Vis $\lambda_{max}$ (nm) MeOH: 416, 607, 653; Ga-POR: UV Vis $\lambda_{max}$ (nm) CHCl3: 394, 397, 489, 525, 561; Ga-UPI: WV-Vis $\lambda_{max}$ (nm) DMF: 405, 537, 574; Ga-UPIII: UV-Vis $\lambda_{max}$ (nm) MeOH: 405, 536, 572; Ga-COPI: WV-Vis $\lambda_{max}$ (nm) MeOH: 398, 531, 569; Pt_PPIX: UV-Vis $\lambda_{max}$ (nm) DMSO: 393, 511, 548.

Additional MPs useful for inhibition of microorganisms include those with scandium (Sc), titanium (Ti), rubidium (Rb), germanium (Ge) and silicon (Si). These metal ions alone are substantially nontoxic for animals.

The study and synthesis of modified MPs allows the identification of functionally important side chains for these antibacterial agents. The roles of two vinyl and two propionyl groups in antibacterial activity are not yet known. A very large number of porphyrin derivatives are known; the eight carbon atoms in the porphyrin ring can accept methyl, ethyl, hydroxyethyl, vinyl, acetyl and propyl side chains [Smith (1975) supra; Dolphin (1978) supra]. Porphyrin can also accept four additional substitutions at the carbon atoms connecting four pyrrole rings into the porphyrin molecule [Smith (1975) supra; Dolphin (1978) supra]. The data obtained in the present studies indicate that very large alterations in the porphyrin structure destroy the antibacterial activity of Mn-meso-tetra-4-sulfonatophenyl porphine.

The role of different porphyrin side chains in the antibacterial activity of MPs is studied with gallium, manganese and indium derivatives of the following modified porphyrins: coproporphyrin I, coproporphyrin IIIH, uroporphyrin I, deuteroporphyrin IX, etioporphyrin I, hematoporphyrin IX, mesoporphyrin IX, octaethylporphine, porphine, phthalocyanine, purpurin 18, meso-tetra-(4-carboxyphenyl) porphine, meso-tetra-(4-pyridyl) porphine, and meso-tetraphenyl porphine. Modified porphyrin derivatives are purchased from Porphyrin Products, Inc., Logan, Utah. The insertion of manganese and indium into porphyrin derivatives requires lower temperatures than the insertion of gallium (100° C. rather than 180–240° C.). To prevent degradation during the insertion of metals, only manganese and/or indium are used in the synthesis of modified MPs. The antibacterial activity of modified MPs is assessed using S. aureus strain 8325–4 and E. coli (hemR+) bacterial strains and compared with the activities of Mn-IX and/or In-IX.

Iron-containing derivatives of all the modified porphyrins are also synthesized. The ability of S. aureus strain 8325-4 and E. coli (hemR+) to use the different iron-containing modified porphyrins and the iron-protoporphyrin IX (heme) as an iron source are compared [Stojiljkovic et al. (1995) supra; Lewis and Dyer (1995) supra; Stojiljkovic and Hantke (1992) supra]. These experiments reveal which particular MP modifications affect the transport of MP through the heme-specific channel, which is a high affinity uptake system for MP-bacterial target interaction.

Example 5

Preliminary Toxicology Testing

Monolayers of MDCK and Vero cells were incubated with 0.5 mg gallium protoporphyrin IX for 24 hrs in 1 mL DMEM plus 10% fetal calf serum. No visible cytotoxic and/or morphological changes were observed.

Two mice were each injected intraperitoneally with 0.5 mg gallium protoporphyrin IX and observed for 7 days. No change in behavior, eating habits and/or apparent stress or general condition were recorded. The animals were sacrificed, and their internal organs were microscopically examined for signs of inflammation. No visible indications of inflammation were observed.

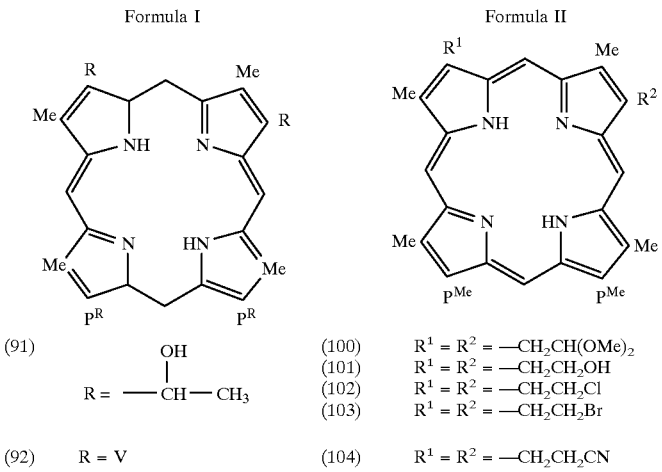

SCHEME 1

-continued

SCHEME 1

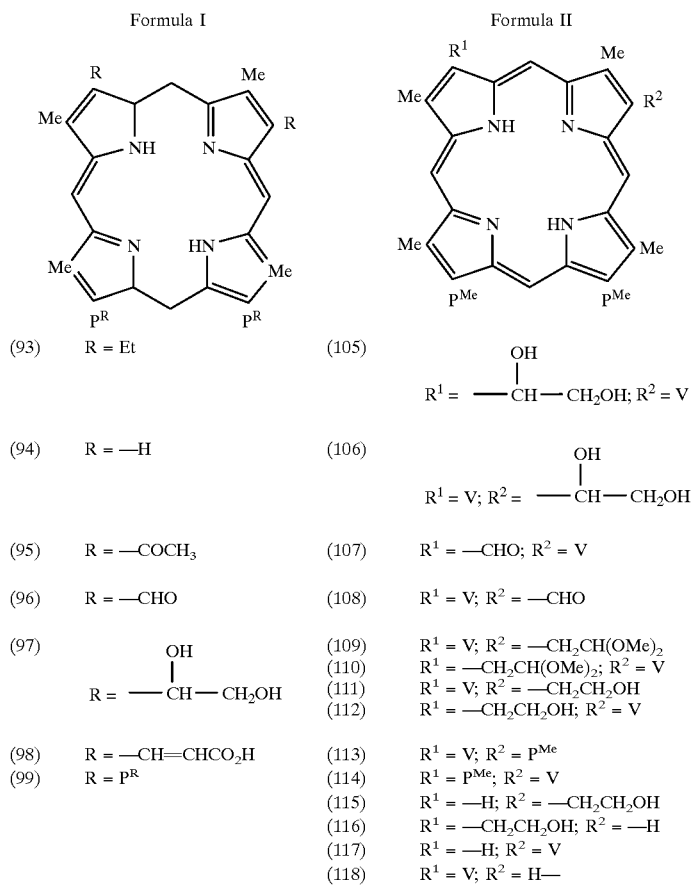

Formula I

(93) R = Et
(94) R = —H
(95) R = —COCH₃
(96) R = —CHO
(97) R = —CH(OH)—CH₂OH
(98) R = —CH=CHCO₂H
(99) R = P$^R$

Formula II (105) R$^1$ = —CH(OH)—CH₂OH; R$^2$ = V
(106) R$^1$ = V; R$^2$ = —CH(OH)—CH₂OH
(107) R$^1$ = —CHO; R$^2$ = V
(108) R$^1$ = V; R$^2$ = —CHO
(109) R$^1$ = V; R$^2$ = —CH₂CH(OMe)₂
(110) R$^1$ = —CH₂CH(OMe)₂; R$^2$ = V
(111) R$^1$ = V; R$^2$ = —CH₂CH₂OH
(112) R$^1$ = —CH₂CH₂OH; R$^2$ = V
(113) R$^1$ = V; R$^2$ = P$^{Me}$
(114) R$^1$ = P$^{Me}$; R$^2$ = V
(115) R$^1$ = —H; R$^2$ = —CH₂CH₂OH
(116) R$^1$ = —CH₂CH₂OH; R$^2$ = —H
(117) R$^1$ = —H; R$^2$ = V
(118) R$^1$ = V; R$^2$ = H—

V = vinyl
E+ = ethyl
P$^R$ = CH₂CH₂CO₂R,
R = H, alkyl, alkoxyl, alkenyl or alkynyl, all from $C_1$ to $C_8$, but preferably H.
Me = methyl

TABLE 1

Susceptibility of different bacteria and yeasts to AMPs

| ORGANISM | Mn-meso | Fe | Pd | Ga | Ru | Mn | Sn | Zn | Mg | In | Tl | Co | Cr |
|---|---|---|---|---|---|---|---|---|---|---|---|---|---|
| Y. enterocolitica | – | + | ND | 28 | – | 30 | – | – | – | 12 | – | – | – |
| N. meningitidis | – | + | – | 24 | 11 | 18 | – | 10 | – | ND | – | – | – |
| S. marcescens | – | ND | – | 23 | – | – | – | – | ND | ND | ND | – | – |
| E. coli | – | + | – | 24 | ND | – | ND | ND | – | – | – | ND | ND |
| P. mirabilis | – | ND | – | 21 | ND | 22 | ND | ND | – | 9 | – | ND | ND |
| K. pneumoniae | – | ND | – | 22 | ND | – | ND | ND | – | 9 | – | ND | ND |
| K. oxytoca | – | ND | – | 21 | ND | – | ND | ND | – | 9 | – | ND | ND |
| Ps. aeruginosa | – | ND | – | – | – | – | – | – | – | – | – | – | – |
| C. freundii | – | + | – | 22 | ND | 22 | ND | ND | – | 9 | – | ND | ND |
| E. aerogenes | – | ND | – | 22 | ND | – | ND | ND | – | 9 | – | ND | ND |
| F. menigosepticum | – | ND | – | 22 | – | 17 | ND | ND | – | – | – | ND | ND |
| S. aureus | – | + | – | 22 | 12 | 23 | – | 12 | 15 | 15 | – | 15 | 10 |
| B. subtilis | – | + | ND | 24 | – | 25 | – | – | 15 | ND | 12 | – | – |
| S. pyogenes A | ND | + | ND | – | ND | – | – | ND | ND | 13 | ND | – | – |
| E. faecalis | ND | ND | – | – | – | – | – | – | – | – | – | – | – |
| M. smegmatis | ND | + | ND | 25 | – | 25 | – | – | ND | ND | ND | – | – |
| M. bovis | ND | ND | – | 35 | – | 35 | – | – | ND | ND | ND | – | – |
| M tuber. H37Rv | – | ND | ND | 20 | ND | – | ND | ND | ND | – | ND | ND | ND |

TABLE 1-continued

Susceptibility of different bacteria and yeasts to AMPs

METALLOPORPHYRINS

| ORGANISM | Mn-meso | Fe | Pd | Ga | Ru | Mn | Sn | Zn | Mg | In | Tl | Co | Cr |
|---|---|---|---|---|---|---|---|---|---|---|---|---|---|
| M tuber. H37Pa | – | ND | ND | 36 | ND | – | ND | ND | ND | 17 | ND | ND | ND |
| S. crevisieae | ND | + | ND | – | – | – | – | – | ND | ND | ND | 18 | – |

N = not determined.
– = resistant.
Sensitivity is expressed as a number corresponding to the diameter (mm) of the inhibition zone.
Mn-meso, Mn-meso-tetra(4-sulfonatophenyl)-porphine chloride.
Sensitivity testing was carried out as described in Example 1.

TABLE 2

Minimal inhibitory concentrations (MIC) expressed in µg/ml of 18 different MPs against representatives of Gram-negative bacteria (Y. enterocolitica fur mutant H1852), Gram-positive bacteria (methicillin-resistant S. aureus IR219) and acid-fast bacilli (M. smegmatis LR222). Bacteria were grown in Nutrient broth (Y. enterocolitica and S. aureus) or in LB + Tween 80 (M. smegmatis). Schematic representation of Ga-PPIX and protoporphyrin IX are also shown

|  | Ga-PPIX | Fe-PPIX | Mg-PPIX | Co-PPIX | Cr-PPIX | Mn-PPIX | Ag-PPIX | Pd-PPIX | Sn-PPIX |
|---|---|---|---|---|---|---|---|---|---|
| Y. enterocolitica | 0.4 | >40 | >40 | 20 | 20 | 0.4 | 20 | >40 | 20 |
| S. aureus | 1.6 | >40 | >10 | 40 | >40 | 3.2 | 40 | 50 | >40 |
| M. smegmatis | 0.4 | >40 | 20 | 20 | 20 | 0.8 | 20 | 20 | 20 |

|  | Zn-PPIX | In-PPIX | SbO-PPIX | Cu-PPIX | Ni-PPIX | Pt-PPIX | Gd-PPIX | Ru-PPIX | Ti-PPIX |
|---|---|---|---|---|---|---|---|---|---|
| Y. enterocolitica | >40 | 0.2 | 20 | 20 | >40 | 30 | 5 | >40 | >40 |
| S. aureus | 3.2 | 1.6 | 40 | >40 | >40 | 40 | ND | 5 | 40 |
| M. smegmatis | 20 | 0.4 | 20 | 20 | 20 | 20 | ND | 20 | >40 |

TABLE 3

Minimal bactericidal concentrations (MBCs) of different MPs against Y. enterocolitica, S. aureus and M. smegmatis

|  | GD-PPIX | GA-PPIX | GA-OEPIX | OEPI | GA-UPI-IX | UPI-IX | Ru-PPIX | PPIX | GA-MPIX | MPIX | IN-PPIX | GA-CHl$_{e6}$ |
|---|---|---|---|---|---|---|---|---|---|---|---|---|
| Y. enterocolitica | 10 | 6.4* | >20 | 5 | 10 | 5/10 | >40 | >40 | 5 | >10 | >13 | 10 |
| S. aureus | ND | >13 | 5 | 5/10 | 10 | 20 | 10 | >40 | >13 | >13 | >13 | ND |
| M. smegmatis | ND | 10 | 10 | 10 | 10 | 10 | >20 | >20 | 10 | >40 | 10 | ND |

MBC were determined by plating bacterial cultures that have been incubated in the presence of MPs at concentrations higher than MIC. MBC was defined as a concentration of a particular MP which reduces the plating efficiency more than 99.9%. Experiments were done with minimal exposure to light (addition of porphyrins waa done in the presence of artifical light).
*Bacteria could be rescued by diluting the culture 100-fold before plating.
ND = not done.

TABLE 4

MICS of Ga-, Mn- and In- protoporphyrins against different bacteria

| | COMPOUND (MIC in µg/ml) | | |
|---|---|---|---|
| ORGANISM | Ga-IX | Mn-IX | In-IX |
| Y. enterocolitica WA-1 | <0.1 | 1 | ND |
| Y. pseudotuberculosis YP66 | <0.1 | <0.1 | ND |
| Neisseria meningitidis | <0.1 | 2 | ND |
| Bacillus subtilis | <0.1 | 1 | ND |
| Staphylococcus aureus 8325-4 | <0.1 | 1 | ND |
| Streptococcus pyogenes JRS4 | >4 | >4 | 0.1 |
| Mycobacterium smegmatis LR222 | 0.5 | 0.5 | ND |
| Mycobacterium bovis (BCG) | 0.4 | 0.8 | ND |

| | |
|---|---|
| S | sensitive; |
| ND | not determined; |
| Ga-IX | gallium-protoporphyrin IX; |
| Mn-IX | manganese-protoporphyrin IX; |
| In-IX | indium-protoporphyrin IX; |
| MIC | minimal inhibitory concentration. |

TABLE 5

MIC of Ga-PPIX and Mn-PPIX against different bacterial isolates. Only *Y. enterocolitica* and *Y. pseudotuberculosis* were grown in iron restricted media (NBD 0.1 mM); Bacterial growth was recorded after overnight incubation (20 to 24 hours; 48 hoursd in the case of *M. smegmatis*; two weeks in the case of *M. bovis*).

| ORGANISM MIC($\mu$g/ml) | Ga-PPIX | Mn-PPIX |
|---|---|---|
| *S. aureus* 8325-4 | 1–2 | 3 |
| *Y. enterocolitica* WA-C | 0.4 | 1–2 |
| *Y. pseudotuberculosis* | 0.2/0.4 | 1–2 |
| *N. meningitidis* IR1072 | 0.1 | 2 |
| *N. gonorrhoeae* MS111 | 0.1 | ND |
| *M. bovis* (BCG) | 0.4 | 0.8 |
| *B. subtilis* 3G18 | 0.2 | 1 |
| *L. monocytogenes* | 0.2 | ND |
| *S. pyogenes* JRS4 | >4 | >4 |
| *M. avium* ATCC15769 | 1 | ND |
| *M. tuberculosis* Rv | 4 | ND |
| *H. pylori* ATCC 43504 | 0.2 | ND |

ND = Not done
GaPPIX = gallium-protoporphyrin IX
MN-PPIX = manganese-protoporphyrin IX

TABLE 6

MPs are transported by heme specific uptake systems

| ORGANISM | COMPOUND (MIC) | | |
|---|---|---|---|
| | Ga-IX | Mn-IX | Heme util. |
| *Y. pseudotuberculosis* YP66 | 0.2–0.4 | 1–2 | +++ |
| *Y. enterocolitica* WA-1(hemR+) | 0.4 | 1–2 | +++ |
| *Y. enterocolitica* hemR– | >10 | >10 | – |
| *Y. enterocolitica* hemT– | <0.1 | ND | +++ |
| *Y. enterocolitica* hemU– | <0.1 | ND | –/+ |
| *Y. enterocolitica* hemV– | <0.1 | ND | –/+ |
| *E. coli* DH-5 alpha hemA | >10 | >10 | – |
| *E. coli* dh-5 alpha hemA(hemR+) | <0.1 | ND | +++ |
| *S. aureus* 8325-4 | 1–2 | 3 | +++ |

MICS were determined as described in Example 1 hereinabove.
Heme utilization was determined as previously described.

TABLE 7

Minimal inhibitory concentrations (MIC) of Ga-PPIX against *E. coli* ndh, ccm, and cytochrome cyo and cyd mutants.

| STRAIN GENOTYPE | MIC Ga-PPIX [$\mu$g/ml] | |
|---|---|---|
| *Escherichia coli*-K12 | NB | NBD[50 $\mu$M] |
| GR70N w.t.* | 10 | 10 |
| GO103 GR70N, ΔcydAB$^r$::Km$^r$ | 10 | 6.4 |
| GP104 GR70N, ΔcyoABCDE::Km$^r$ | 10 | 10 |
| MWC215 GR70N, ndh::Cm$^r$ | 10 | 10 |
| EC06 MC1061, ΔccmABCDEFGH | >20 | >20 |
| IR2976 EC06 [phemR$^+$] | >30 | 0.5 |
| IR2897 GR70N [phemR$^+$] | >10 | <0.1 |

TABLE 7-continued

Minimal inhibitory concentrations (MIC) of Ga-PPIX against *E. coli* ndh, ccm, and cytochrome cyo and cyd mutants.

| STRAIN GENOTYPE | MIC Ga-PPIX [$\mu$g/ml] | |
|---|---|---|
| *Escherichia coli*-K12 | NB | NBD[50 $\mu$M] |
| IR2898 GO103 [phemR$^+$] | <0.2 | <0.02 |
| IR2885 GO104 [phemR$^+$] | <0.2 | <0.02 |
| IR2899 MWC215 [phemR$^+$] | >10 | <0.1 |

* = Full genotype of the strain GR70N is F- thi rpsL gal
phemR = plasmid pT7-5 expressing the hemR gene.
Experiments were repeated at least five times.

TABLE 8

MICs of Ga-UPI against selected clinical yeast isolates. Growth was scored after 24 and 48 hours of incubation.

| STRAIN | MIC 80 Ga-UPI I[$\mu$g/ml] Microdilution | |
|---|---|---|
| | 24 hours | 48 hours |
| *Candida albicans* | | |
| 97-010 | 2 | 8 |
| 97-012 | 2 | 8 |
| 97-014 | 2 | 8 |
| 97-015 | 2 | 8 |
| 97-031 | 2 | 16 |
| *Candida krusei* | | |
| 97-058 | 1 | 4 |
| 97-059 | 2 | 8 |
| ATCC-6258 | 1 | 2 |
| *Candida pillosus* | | |
| 97-056 | 1 | 2 |
| 97-057 | 2 | 8 |
| *Cryptococcus neoformans* * | | |
| 97-044 | 16 | 16 |
| 97-045 | 16 | 32 |
| 97-046 | 16 | 16 |
| 97-047 | 8 | 16 |
| 97-048 | 16 | 16 |
| *Candida glabrata* | | |
| 97-049 | 8 | 32 |
| 97-050 | 8 | 16 |
| 97-051 | 8 | 32 |
| 97-052 | 8 | 32 |
| 97-053 | 8 | 16 |
| *Candida tropicalis* | | |
| 97-054 | 16 | 32 |
| 97-055 | 8 | 16 |

TABLE 9

Bacterial strains and plasmids used in the study

| | RELEVANT GENOTYPE | SOURCE/REFERENCE |
|---|---|---|
| BACTERIA | | |
| *Escherichia coli* | | |
| DH5-alpha | | Stratagene |
| IR1532 | DH5-alpha but heme biosyn. m. | (Stojiljkovic and Srinivasan, 1997) |
| GR70N | str$^r$ gal thi | (Calhoun et al. 1993) |
| GO103 | GR70N but Δcyd::kan$^r$ | (Calhoun et al. 1993) |
| GO104 | GR70N but Δcyo::kan$^r$ | (Calhoun et al. 1993) |
| MWC215 | wild type but ndh::cm$^r$ | (Calhoun et al. 1993) |
| EC06 | MC1061, but ΔccmABCDEFGH | (Thöny-Meyer et al. 1995) |
| *Y. enterocolitica* WA-C | | |
| H1883 | plasmidless strain, hemPRSTVU+ | (Stojiljkovic and Hantke, 1992) |
| H1852 | WA-C but fur-5 | K. Hantke |
| H2000 | WA-C but tonB– | (Koebnik et al. 1993) |
| WA-C 103 | WA-C but hemR– | (Stojiljkovic and Hantke, 1994) |
| WA-C 120 | WA-C but hemT– | (Stojiljkovic and Hantke, 1994) |
| WA-C 109 | WA-C but hemU– | (Stojiljkovic and Hantke, 1994) |
| WA-C 144 | WA-C but hemV– | (Stojiljkovic and Hantke, 1994) |
| *Y. pseudotuberculosis* pYVII6 | | J. Bliska |
| *N. meninigitidis* IR1072 | | (Stojiljkovic et al. 1995) |
| *N. gonorrhoeae* MS11 | | Lab. collection |
| *B. subtilis* 3G18 | trp C2 ade met | L. Hederstedt |
| *S. aureus* 8325-4 | | Lab. collection |
| *S. aureus* IR2419 | clinical isolate, methicillinR | R. Nolte |
| *S. carnosus* TM300 | | K. Hantke |
| *S. xylolus* C20a | | K. Hantke |
| *S. pyogenes* JRS-4 | | J. Scott |
| *E. faecalis* | | J. Scott |
| *L. monocytogenes* | | K. Ziegler |
| *M. smegmatis* LR22 | | G. Churchward |
| *M. bovis* | | G. Churchward |
| PLASMIDS | | |
| pT76.91 | hemPR | (Stojiljkovic and Hantke, 1992) |

TABLE 10

MICs of different modified porphyrins and MPs against Gram-negative and -positive bacteria, and acid-fast bacilli.

| | GA-POR | POR | GA-PP-IX | PP-IX | GA-MP-IX | MP-IX | GA-OEP | OEP | GA-C$_{e6}$ | C$_{e6}$ | UP-1 |
|---|---|---|---|---|---|---|---|---|---|---|---|
| *Y. enterocolitica* H1852 [fur-5] | 20 | 30 | 0.4 | 30 | 2.5 | 2.5 | 20 | 5 | 5 | 20 | 10 |
| *Y. enterocolitica* WA-C103 [hemR] | 20 | 20 | 10 | >10 | 5 | 20 | 20 | 10 | 10 | >10 | 10 |
| *S. aureus* IR2419 | 50 | 50 | 1.6 | 50 | 1.6 | 20 | 10 | 10 | 3.2 | 20 | 20 |
| *M. segmatis* LR222 | 5 | >40 | 0.4 | >40 | 0.4 | >40 | 5 | 10 | 0.4 | 20 | 20 |

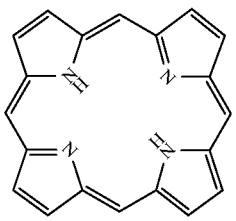

TABLE 10-continued
MICs of different modified porphyrins and MPs against Gram-negative and -positive bacteria, and acid-fast bacilli.
GA-POR  POR  GA-PP-IX  PP-IX  GA-MP-IX  MP-IX  GA-OEP  OEP  GA-C$_{e6}$  C$_{e6}$  UP-1
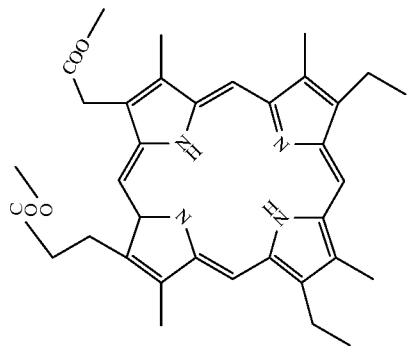
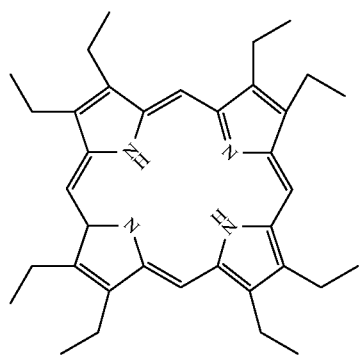
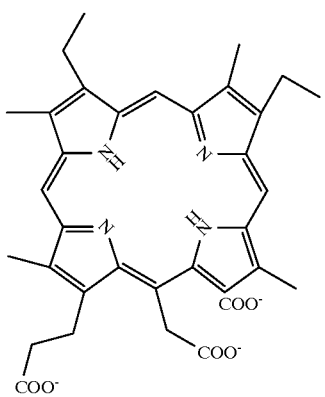

TABLE 10-continued

MICs of different modified porphyrins and MPs against Gram-negative and -positive bacteria, and acid-fast bacilli.

GA-POR   POR   GA-PP-IX   PP-IX   GA-MP-IX   MP-IX   GA-OEP   OEP   GA-$C_{e6}$   $C_{e6}$   UP-1

POR = porphine
MPIX = mesoporphyrin IX
OEP = octaethylporphine
UPI = uroporphyrin I.
Incubations were carried out in the dark to avoid phototoxic effects which could contribute to the activity of the iron-free porphyrins reported by Nitzan et al. (1987) vide infra.

TABLE 11

Ability of heme (Fe-PPIX) and protoporphyrin IX (PPIX) excess to counteract antibacterial activity of Ga-PPIX against *Y. enterocolitica*, *M. smegmatis* and *S. aureus*.

|  | PPIX [µg/ml] | | | | Fe-PPIX [µg/ml] | | | |
| --- | --- | --- | --- | --- | --- | --- | --- | --- |
|  | 1 | 10 | 20 | 100 | 1 | 10 | 20 | 100 |
| *M. smegmatis* | | | | | | | | |
| +1 µg/ml Ga-PPIX | − | −/+ | + | + | − | − | − | − |
| −1 µg/ml Ga-PPIX | + | + | + | + | + | + | + | + |
| *Y. enterocolitica* | | | | | | | | |
| +1 µg/ml Ga-PPIX | − | − | − | − | − | + | + | + |
| −1 µg/ml Ga-PPIX | + | + | + | − | + | + | + | + |
| *S. aureus* | | | | | | | | |
| +1 µg/ml Ga-PPIX | − | − | − | + | − | − | − | − |
| −1 µg/ml Ga-PPIX | + | + | + | + | + | + | + | + |

+ = growth
− = no growth

What is claimed is:

1. A method for inhibiting growth of a microorganism, said method comprising the step of administering an effective amount of a composition comprising a non-iron metalloporphyrin, wherein said metalloporphyrin has a porphyrin structure as given in Formula I or Formula II, and a non-iron metal ion complexed therewith, wherein the metal ion is selected from the group consisting of a gallium ion, an indium ion, manganic ion, ruthenium ion, a copper ion and a gadolinium ion.

2. The method of claim 1 wherein the microorganism whose growth is inhibited is a bacterium.

3. The method of claim 2 wherein the bacterium expresses a heme uptake system.

4. The method of claim 3 wherein the bacterium is a gram-negative bacterium.

5. The method of claim 4 wherein the gram-negative bacterium is a member of a genus including Escherichia, Campylobacter, Neisseria, Hemophilus, Yersinia, Klebsiella, Enterobacter, Helicobacter, Vibrio, Plesiomonas, Legionella, Shigella, Aeromonas, Plesiomonas and Proteus.

6. The method of claim 3 wherein the bacterium is a gram-positive bacterium.

7. The method of claim 6 wherein the bacterium is a member of the genus Staphylococcus, Peptostreptococcus, or Bacillus, or Listeria.

8. The method of claim 3 wherein the bacterium is an acid-fast bacterium.

9. The method of claim 8 wherein the acid-fast bacterium is a member of the genus Mycobacterium.

10. The method of claim 1 wherein the microorganism whose growth is inhibited is a fungus or yeast.

11. The method of claim 1 wherein the fungus or yeast whose growth is inhibited is a member of the genus Candida, Saccharomyces or Cryptococcus.

12. The method of claim 1 wherein the non-iron metalloporphyrin is protoporphyrin IX complexed with a metal ion.

13. The method of claim 12 wherein the non-iron metal ion is selected from the group consisting of a gallium (+3) ion, an indium (+3) ion and a manganese (+2) ion.

14. The method of claim 13 wherein said metal ion is a gallium (+3) ion.

15. The method of claim 1 wherein said metalloporphyrin is uroporphyrin complexed with a metal ion selected from the group consisting of gallium, indium and manganese ions.

16. The method of claim 15 wherein said metal ion is a gallium (+3) ion.

17. The method of claim 1 wherein said metalloporphyrin is mesoporphyrin IX complexed with a metal ion selected from the group consisting of gallium, indium and manganese ions.

18. The method of claim 17 wherein said metal ion is a gallium (+3) ion.

19. The method of claim 1 wherein said metalloporphyrin is octaethylporphyrin IX complexed with a metal ion selected from the group consisting of gallium, indium and manganese ions.

20. The method of claim 19 wherein said metal ion is a gallium (+3) ion.

* * * * *

UNITED STATES PATENT AND TRADEMARK OFFICE
CERTIFICATE OF CORRECTION

PATENT NO. : 6,066,628
DATED : May 23, 2000
INVENTOR(S) : Stojiljkovic and Churchward Page 1 of 4

It is certified that error appears in the above-identified patent and that said Letters Patent is hereby corrected as shown below:

In the Specification:

Column 13,
Line 15, before "2.91" delete "5" and replace with -- δ --.
Line 22, delete "WV-Vis" and replace with -- UV-Vis --.
Line 24, delete "WV-Vis" and replace with -- UV-Vis --.

Columns 17 and 18,
Table 2, 3rd line of the header, delete "IR219" and replace with -- IR2419 --.
Table 3, 4th column heading, delete "OEPI" and replace with -- OEPIX --.

Column 21,
Table 9, 3rd reference from the bottom, delete "M. smegmatis LR22" and replace with -- M. smegmatis LR222 --.

In Table 10, insert labels below the structures as follows:
At columns 21 and 22, label the structure -- POR --.
At columns 23 and 24, label the first structure -- MP-IX --.
At columns 23 and 24, label the second structure -- OEP --.
At columns 23 and 24, label the third structure -- Chlorin e6 --.
At columns 25 and 26, label the structure -- UP-1 --.

Add the following publications to the References Cited:

Bramanti, T.E. and Holt, S.C. "Hemin uptake in Porphyromonas gingivalis: Omp26 is hemin-binding surface protein" J. *of Bacteriology* 175(22):7413-7420 (1993)

Cannon, J.B. "Pharmaceutics and Drug delivery aspects of heme and porphyrin therapy" J. *of Pharm. Sciences* 82(5):435-445 (1993)

Cope, L.D. et al. "The 100Da haem:haemopexin-binding protein of Haemophilus influenzae: structure and localization" *Mol. Microbiology* 13(5):863-873 (1994)

Cornelissen, C.N. and Sparling, P.F. "Iron piracy: acquisition of transferrin-bound iron by bacterial pathogens" Mol. *Microbiology* 14(5):843-850 (1994)

Coutsolelos, A and Guilard, R. "Synthese et caracteristiques physicochimiques de gallioporphyrines a liason σ metal-carbone" J. *of Organ. Chem.* 253:273-282 (1983)

UNITED STATES PATENT AND TRADEMARK OFFICE
CERTIFICATE OF CORRECTION

PATENT NO. : 6,066,628
DATED : May 23, 2000
INVENTOR(S) : Stojiljkovic and Churchward It is certified that error appears in the above-identified patent and that said Letters Patent is hereby corrected as shown below:

Desai, P.J. et al. "Binding and accumulation of hemin in Neisseria gonorrhoeae" *Infection and Immunity* 63(12):4634-4641 (1995)

Falk, J.E. *Porphyrins and Metalloporphyrins* ©1975 Elsevier Scientific Publishing Co., Amsterdam, Ed. Smith, K.M. pp 29-58, 123-153, 729-754

Hansson, M. et al. "The Bacillus subtilis hemAXCDBL gene cluster, which encodes enzymes of the biosynthetic pathway from glutamate to uroporphyrinogen III" *J. of Bacteriology 173(8):2590-2599 (1991)*

Henderson, D.P. and Payne, S.M. "Characterization of the Vibrio cholerae outer membrane heme transport protein HutA: Sequence of the gene, regulation of expression, and homology to the family of TonB-dependant proteins" *J. of Bacteriology 176 (11):3269-3277 (1994)*

Henderson, D.P. and Payne, S.M. "Cloning and characterization of the Vibrio cholerae genes encoding the utilization of iron from haemin and haemoglobin" *Mol. Microbiology 7(4):461-469 (1993)*

Hughes, T.E. and Hansen, L.A. "Gallium Nitrate" *Ann. of Pharmacotherapy 26:354-362 (1992)*

Kafala, B. and Sasarman, A. "Cloning and sequence analysis of the hemB gene of Staphylococcus aureus" *Can. J. Microbiol. 40:651-657 (1994)*

Koebnik, R., et al. "The TonB protein of Yersinia enterocolitica and its interactions with TonB-box proteins" Mol. *Gen. Genet. 237:152-160 (1993)*

Lee, B.C. "Isolation of haemin-binding proteins of Neisseria gonorrhoeae" *J. Mol. Microbiol.36:121127 (1992)*

Letoffe, S., et al. "Iron acquisition from heme and hemoglobin by a Serratia marcescens extracellular protein" Proc. *Natl. Acad. Sci. USA. 91:9876-9880 (1994)*

Liochev, S.I. and Fridovich, I. "A cationic manganic porphyrin inhibits uptake of paraquat by Escherichia coli" *Archives of Biochem. and Biophys. 321(1):271-275 (1995)*

UNITED STATES PATENT AND TRADEMARK OFFICE
CERTIFICATE OF CORRECTION

PATENT NO.   : 6,066,628
DATED        : May 23, 2000
INVENTOR(S)  : Stojiljkovic and Churchward It is certified that error appears in the above-identified patent and that said Letters Patent is hereby corrected as shown below:

Malik, Z. et al. "The bactericidal activity of a deuteroporphyrin-hemin mixture on gram-positive bacteria. A microbiological and spectroscopic study" *J. of Photochem. and Photobiol. B: Biology* 6:419-430 (1990)

Massad, G. et al. "Acquisition of iron from host sources by mesophilic Aeromonas species" J. of *Gen. Microbiol.* 137:237-241 (1991)

Nitzan, Y. et al. "Characterization of hemin antibacterial action on Staphylococcus aureus" *FEMS Microbiol. Lett.* 48:401-406 (1987)

Nitzan, Y., et al. "Growth-inhibitory effect of hemin on Staphylococci" *Current Biocrobiol.*, 14:279284 (1987)

Otto, B.R., et al. "Transferrins and Heme-compounds as iron sources for pathogenic bacteria" *Crit. Rev. in Microbiol.* 18(3):217-233 (1992)

Padmanaban, G., et al. "Haem as a multifunctional regulator" *TIBS* 14:492-496 (1989)

Pratviel, G., et al. "Mechanism of DNA cleavage by cationic manganese porphyrins: Hydroxylations at the 1'-carbon and 5'-carbon atoms of deoxyriboses as initial damages" Nucleic Acids *Res.* 19(22):6283-6288 (1991)

Stojiljkovic, I. and Hantle, K. "Hemin uptake system of Yersinia enterocolitica: similarities with other TonB-dependent systems in Gram-negative bacteria" *EMOB J.* 11(12):4359-4367 (1992)

Stojiljkovic, I. and Hantke, K. "Transport of haemin across the cytoplasmic membrane through a haemin-specific periplasmic binding-protein-dependent transport system in Yersinia enterocolitica" *Mol. Microbiol.* 13(4):719-732 (1994)

Stojiljkovic, I. et al. "The Neisseria meningitidis haemoglobin receptor: its role in iron utilization and virulence" Mol. *Microbiol.* 15(3):531-541 (1995)

Stojiljkovic, I., et al. HmbR outer membrane receptors of pathogenic neisseria spp.: Iron-regulated, hemoglobin-binding proteins with a high level of primary structure conservation" J. of *Bacteriol.* 178(15):4670-4678 (1996)

UNITED STATES PATENT AND TRADEMARK OFFICE
CERTIFICATE OF CORRECTION

PATENT NO. : 6,066,628
DATED : May 23, 2000
INVENTOR(S) : Stojiljkovic and Churchward It is certified that error appears in the above-identified patent and that said Letters Patent is hereby corrected as shown below:

Weinberg, E.D. "Iron withholding: A defense against infection and neoplasia" *Physiological Rev.* 64(1):65-102 (1984)

Bernadou, J. et al. "Potassium Monopersulfate and a Water-Soluble Manganese Porphyrin Complex [Mn(TMPyP)](OAc), as an Efficient Reagent for the oxidative Cleavage of DNA" *Biochemistry* 28:7268-7275 (1989)

Celebuski et al., "Chemical modification of erythromycin: novel reaction observed by treatment with metalloporphyrins" *Tetrahedron Letters* 35(23):3837-3840 (1994)

Macquet, J.P. and Theophanides, T. "Complexes d'hematoporphyrine IX avec le platine (II)[1]: synthese, intermediaires, spectres, interet biologique" Can. *J. Chem.* 51:219 (1972)

Sheth, A. et al. "Solution Conformation of D-CTCGAGCTCGAG by Two-Dimensional NMR: Conformational Heterogeneity at XhoI Cleavage Site" *Biochemistry* 28:7275-7282 (1989)

Add the following to the References Cited, Foreign Patent Documents:

JP 08266604 A2    15.10.96    Japan
JP 01124460 A2    17.05.89    Japan

Signed and Sealed this

Fourth Day of September, 2001

*Attest:*

*Attesting Officer*

NICHOLAS P. GODICI
*Acting Director of the United States Patent and Trademark Office*